United States Patent [19]

Desmond et al.

[11] Patent Number: 4,766,265

[45] Date of Patent: Aug. 23, 1988

[54] CATALYSTS FOR THE CONVERSION OF ETHANE TO LIQUID AROMATIC HYDROCARBONS

[75] Inventors: Michael J. Desmond, Cleveland Heights, Ohio; Joann Henry, Greenwood, Ind.

[73] Assignee: The Standard Oil Company, Cleveland, Ohio

[21] Appl. No.: 59,433

[22] Filed: Jun. 8, 1987

[51] Int. Cl.$^4$ .............................................. C07C 12/02
[52] U.S. Cl. ................... 585/415; 585/417; 585/418; 585/419
[58] Field of Search ............... 585/415, 417, 418, 419

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/328 |
| 4,120,910 | 10/1978 | Chu | 260/673 |
| 4,157,293 | 6/1979 | Plank et al. | 585/418 |
| 4,180,689 | 12/1979 | Davies et al. | 585/415 |
| 4,350,835 | 9/1982 | Chester et al. | 585/415 |
| 4,392,989 | 7/1983 | Chu et al. | 252/455 |
| 4,417,083 | 11/1983 | Bernard et al. | 585/419 |
| 4,543,347 | 9/1985 | Heyward et al. | 502/61 |
| 4,565,897 | 1/1986 | Gane et al. | 585/415 |
| 4,613,716 | 9/1986 | McNiff | 585/415 |
| 4,642,403 | 2/1987 | Hyde et al. | 585/415 |
| 4,654,316 | 3/1987 | Barri et al. | 502/61 |
| 4,654,454 | 3/1987 | Barri et al. | 585/415 |

FOREIGN PATENT DOCUMENTS 0050021  4/1982  European Pat. Off. .

*Primary Examiner*—Asok Pal
*Attorney, Agent, or Firm*—Sue E. Phillips; Joseph G. Curatolo; Larry W. Evans

[57] ABSTRACT

The invention relates to a process for the conversion of ethane to liquid aromatic hydrocarbons comprising contacting, at a temperature of from about 500° C. to about 700° C., an ethane rich feedstock with a catalyst comprising a gallium modified molecular sieve catalyst, promoted with rhenium and a metal selected from the group consisting of nickel, palladium, platinum, rhodium and iridium.

19 Claims, No Drawings

CATALYSTS FOR THE CONVERSION OF ETHANE TO LIQUID AROMATIC HYDROCARBONS

FIELD OF THE INVENTION

The invention relates to the conversion of ethane to liquid aromatics by bringing the feedstock into contact with an aluminosilicate-, gallosilicate-, or borosilicate-supported catalyst.

BACKGROUND

The conversion of light hydrocarbons to aromatics is best viewed as a hydrogen disproportionation reaction. For each aromatic molecule formed, a significant number of hydrogen equivalents are generated. The thermodynamics of the disproportionation reaction dictate that the reaction should proceed such that more mass is converted to fuel gases than to liquid aromatic products. Therefore, catalysts which promote the formation of molecular hydrogen, which in turn promotes liquid aromatic production are desired. The production of liquid aromatic products represents the production of premium products from a fuel or chemical standpoint.

The conversion of light hydrocarbons to aromatic hydrocarbons over modified ZSM-5 systems, which are acidic molecular sieves, is known. Catalysis over molecular sieves involves the diffusion of reactants into the microporous channel system of the molecular sieve and the diffusion of the products out of the same system. Modified ZSM-5 zeolite catalysts have been used to catalyze both paraffin dehydrogenation and olefin dehydrocyclooligomerization. These catalysts provide shape selectivity such that large fractions of $C_{10}+$ products are avoided. Various modifications and pre-treatments of the zeolite catalyst have resulted in improvements in light hydrocarbon conversion and aromatic selectivity, though often one has been achieved to the slight detriment of the other.

Ethane conversion processes disclosed in existing art are very similar to one another in nature: a ZSM-5 zeolite in the acid form is modified with zinc and/or gallium to act as a catalyst for the formation of aromatics from ethane at temperatures near 600° C. Most of the examples of ethane conversion over ZSM-5 catalysts in the patent literature disclose a ZSM-5 catalyst synthesized under agitated conditions to form the intermediate gel phase. This produces submicron crystalline size in the resultant molecular sieve, which tends to cause severe coking of the catalyst.

In early 1986, the art reported maximum per pass conversions (ppc) of light hydrocarbons to aromatics of about 20%. Patents to Mobil, specifically U.S. Pat. Nos. 4,120,910 and 4,350,835, disclose dramatic changes in per pass conversion depending on run time, i.e. 21% ppc at 10 minutes over a CuZnZSM-5 and 11.2% ppc at 40 minutes over the same catalyst. A later patent, to British Petroleum, EP 0 171 981, reported conversion of ethane to aromatics over a simple GaZSM-5 catalyst at high temperatures and relatively low space velocity.

A more recent patent is U.S. Pat. No. 4,613,716, to British Petroleum, disclosing and claiming a GaHZSM-5 catalyst treated with either a Group VIIB or a Group VIII metal promoter for ethane conversion. This art reports slightly improved per pass conversion of ethane to aromatics, in the 21% to 24% range.

It is an object of the present invention to develop a process for producing an ethane conversion catalyst which effectively and efficiently converts ethane to liquid aromatic hydrocarbons.

It is another object of the present invention to develop a catalyst displaying high conversion rates and maintaining good selectivity to aromatics.

SUMMARY OF THE INVENTION

We have discovered that treatment of the gallium impregnated molecular sieve support catalyst with both rhenium and a metal selected from the group consisting of nickel, palladium, platinum, rhodium and iridium, can further enhance conversion and selectivity of ethane to liquid aromatics. Surprisingly, with certain compositions, the order of promoter addition yields even greater enhancement of conversion and selectivity. With this discovery, it was also observed that methane selectivity was reduced over that of prior art catalyst systems, resulting in per pass conversion of ethane to aromatics in excess of 25%.

The subject invention involves a process for the conversion of ethane to liquid aromatic hydrocarbons comprising contacting, at a temperature of from about 500° C. to about 700° C., an ethane rich feedstock with a catalyst comprising a gallium modified molecular sieve catalyst, promoted with rhenium and a metal selected from the group consisting of nickel, palladium, platinum, rhodium and iridium.

DETAILED DESCRIPTION OF THE INVENTION

The process of the present invention relates to the conversion of ethane to liquid aromatic hydrocarbons. This conversion is accomplished by contacting a hydrocarbon feedstock rich in ethane with a catalyst comprising a modified acid form molecular sieve. The feedstock may be derived from natural gas separation, refinery fuel gas streams, or many other known ethane sources. The feedstock content may range from being 100% ethane, to containing only minor amounts of ethane in a feedstock predominantly of hydrogen, methane, and relatively minor amounts of $C_2$–$C_5$ olefins and $C_3$–$C_5$ paraffins. The feedstock should be essentially free of oxygen-containing species, such as oxygen, water, carbon monoxide, carbon dioxide and other oxygenated organics.

The initial step in the conversion of ethane to liquid aromatics is the dehydrogenation of ethane, precipitated by the activation of existing C—H bonds. The dehydrogenated intermediates then undergo oligomerization and sequential cracking, isomerization, and dehydrocyclization reactions, resulting in a product rich in aromatics.

The term "molecular sieve" as used herein refers to microporous structures of alumino-, gallo- or borosilicates wherein the gallo- and borosilicates are of the same structure as the corresponding aluminosilicates, which can also be classified as zeolites. Exemplary of these materials are Zeolite ZSM-5 (U.S. Pat. No. 3,702,886) and Zeolite ZSM-11 (U.S. Pat. No. 3,709,979), which are the preferred structures.

The molecular sieves have crystalline, hydrated frameworks, based on a three-dimensional network of $MO_4$, wherein M is aluminum, boron or gallium, and $SiO_4$ tetrahedra, the $MO_4$ and $SiO_4$ being linked to each other by the sharing of oxygens. The Si:M weight or molar ratio in the support material is in the range of about 10:1 to about 100:1, preferably ranging from about 20:1 to about 50:1. The framework contains channels and interconnected voids which are occupied by cations and water molecules. The as-synthesized molecular sieve can contain organic and/or alkali metal cations which are removed prior to catalytic use. The organic cations can be effectively removed during a calcination of the as-prepared molecular sieve, at a temperature of between about 300° and about 700° C., preferably between about 400° and about 600° C., for a period of from about a few hours to about a few days. The alkali metal cations can be effectively removed by ion exchange, such as by treatment of the molecular sieve with a strong acid, and/or by ion exchange with other cations, such as ammonium, zinc, aluminum or gallium. Pretreatment of the molecular sieve in strong acid under reflux, prior to cation exchange or impregnation, is known to further stabilize the catalytic activity. The acid reflux process removes some of the M component from the framework into solution or into the pores of the molecular sieve.

In the preferred embodiment, the molecular sieve is first exchanged with ammonium. The ammonium form is then calcined to generate the acid form of the molecular sieve, for example the HZSM-5 form.

The acid form of the molecular sieve supports are treated with a source of a metal chosen from gallium, aluminum, and/or zinc. The term "treatment" refers to ion exchange, impregnation, gas phase displacement, or any other known method of incorporating the metal into the molecular sieve structure.

The most preferable metal for the exchange or impregnation is gallium, which produces a very active conversion catalyst. The theorized role of the gallium added to the ZSM-5 zeolite is to promote the dehydrogenation of the light hydrocarbon and to modify the acidity of the catalyst such that liquid forming reactions that generate molecular hydrogen as a by-product proceed to a significant extent. The gallium may be present in an amount from about 0.1% to about 10% by weight of the total molecular sieve in the catalyst composition. The gallium is either impregnated or exchanged through a solution of a gallium salt, examples of which include gallium chloride, and gallium nitrate, or oxide complexes generated in strong acid or base solutions.

Once the gallium treatment has been accomplished, the resulting GaHZSM-5 catalyst is then treated such that rhenium and a metal selected from the group consisting of nickel, palladium, platinum, rhodium and iridium, are incorporated therein. Most preferably, the metal utilized in combination with rhenium is platinum or rhodium.

Rhenium is a promoter which is utilized in hydrocarbon conversion reactions to additionally promote the activation of C—H bonds, as well as the isomerization and rearrangement of hydrocarbon molecules. Because of its ability to rearrange and cleave hydrocarbon molecules, rhenium has been determined to be an additional promoter of methane byproduct formation, thereby increasing overall ethane conversion.

The metal component, selected from the group consisting of nickel, palladium, platinum, rhodium and iridium, is theorized to act as a promoter for the dehydrogenation reaction of the oligomerized intermediates formed from ethane during the reaction. The metals unexpectedly enhance the overall selectivity of ethane conversion to the desired aromatics. This results in a decrease in the methane selectivity promoted by the rhenium component. One would expect a corresponding drop in overall conversion with the drop in methane selectivity. To the contrary, however, conversion rates remain high and an increase in selectivity to aromatics is observed.

Any compound may serve as a source of the rhenium or the selected metal to be incorporated, i.e. organometallic compounds, ligand complex compounds, salts, acids, or bases. It is preferable, however, for the rhenium precursor to contain rhenium-oxygen bonds, such as in the acids or salts of the perrhenate anion. Preferred sources of the selected metals are water or polar solvent soluble salts, such as acetates, nitrates, including but not limited to $Rh(NO_3)_3.2H_2O$, or salts of complex cations, including but not limited to $[Pt(NH_3)_4]^{2+}$ and $[Pd(NH_3)_4]^{2+}$ cations.

Rhenium may be present in the catalyst at levels ranging from about 0.1% to about 10% by weight of the total catalyst, preferably from about 0.4% to about 5.0% by weight of the total catalyst. The metals may be incorporated into the catalyst at levels of between about 0.1% to about 25.0% by weight of the total catalyst, preferably from about 0.2% to about 5.0% by weight of the total catalyst.

A binder may be added to aid in fabricating the molecular sieve-supported metal into a suitable form. Binder materials which may be used include clays, alumina, silica and graphite. The finished catalyst may contain binder amounts of between zero and about 95% by weight, more preferably between about 10% and about 50% by weight. The preferred binder material is silica, which can be incorporated in colloidal form from materials such as Ludox TM AS-30 or AS-40, available from DuPont. Silica has been found not to interfere with catalyst activity and additionally does not promote side reactions, such as coking.

The reaction temperature should be maintained between temperatures of from about 500° C. to about 700° C., preferably from 575° C. to 650° C. Pressure is not critical and can be from ambient to about 20 atmospheres, and is preferably from ambient to about 10 atmospheres. The feed rate may range from about 0.1 to about 50 parts by weight ethane to weight of total catalyst per hour (wwh), and is preferably from about 0.1 to about 5 wwh.

EXAMPLES

ZSM-5 Synthesis

The aluminosilicate used as the catalyst support was prepared by combining 525 grams of Ludox TM AS-40 silica sol with 280 grams of tetrapropylammonium bromide, stirring continuously. A second solution, containing sodium hydroxide and water, 42 grams and 158 grams respectively, was also prepared. To the silica sol-tetrapropylammonium bromide solution was added 12 grams of pseudoboehmite (74.2% alumina) and vigorously stirred. While stirring was maintained, the sodium hydroxide solution was added, resulting in immediate gellation of the total mixture. The mixture was stirred until a homogeneous gel suspension was achieved. The suspension was heated in an autoclave at 150° C. for five days. The autoclave was then cooled and the crystalline ZSM-5 aluminosilicate was recovered by filtration, washed vigorously with water and air dried at ambient temperature.

ZSM-5 Pretreatment and HZSM-5 Formation—(Adapted from GB No. 2,117,367A)

A 50 gram portion of the ZSM-5 recovered above was washed with 500 ml of distilled water and filtered, and then washed with 1 liter of 10% $HNO_3$ solution. This acid washed solid was then washed with 1 liter of distilled water, filtered and vacuum dried at 100° C. for 16 hours.

This dried solid was then placed in a muffle furnace, and calcined. The temperature was ramped from room temperature to 500° C. at a rate of 125° C. per hour. The 500° C. temperature was then maintained for 87 hours, after which time the sample was removed and cooled to room temperature.

The calcined zeolite was then refluxed in 1.65 liters of 10% $HNO_3$ for 2.5 hours, then cooled. The solid was recovered by filtration, washed with 1 liter of distilled water and dried under vacuum at 100° C. for 16 hours. The solid was cooled and refluxed for 4 hours in 1.5 liters of a 0.67M solution of ammonium nitrate. The material, now ammonium exchanged, was recovered by filtration and washed with 2 liters of distilled water. It was dried under vacuum at 100° C. for 16 hours. The dried zeolite was placed in a muffle furnace and the temperature was ramped to 500° C. over a 4 hour period, and maintained at 500° C. for 16 hours. The HZSM-5 recovered after this process weighed 34.6 grams and had a Si:Al mole ratio of 24 and a Si:Na mole ratio of 350.

Gallium Exchange to Form GaHZSM-5

A portion of the HZSM-5 was then treated to add the gallium component. The HZSM-5 was placed in a flask containing a 0.065M gallium nitrate solution. The total amount of gallium nitrate was five times the total molar aluminum content of the zeolite. This mixture was refluxed for 4 hours, cooled and filtered. The solid recovered was washed with 2 liters of distilled water and dried under vacuum at 100° C. for 16 hours. The final ratio of Si:Ga in the exchanged material was about 140.

Formation of Bound GaHZSM-5—Catalyst A

The catalyst above was prepared for testing by slurrying it with an equivalent weight of Ludox TM AS-40. This formed a thick paste, which was dried in an oven at 110° C., cooled and broken into pieces. The resultant 10–30 mesh fraction was used for further modification and reaction screening. This was designated as Catalyst A, which was the 10–30 mesh form of the gallium exchanged HZSM-5 zeolite.

Formation of Catalysts B and C

Three samples, 3.0 grams each, of the 10–30 mesh silica bound gallium exchanged HZSM-5 of Catalyst A were impregnated with an alcoholic solution of gallium nitrate nonahydrate at levels corresponding to the addition of up to 1% and 2% by weight of the nonahydrate to the three samples respectively. These samples were oven dried at 125° C., followed by calcination at 500° C. to decompose the nitrates. The resultant catalyst had increased gallium contents of $2.3 \times 10^{-5}$ moles per gram (Catalyst B) and $4.7 \times 10^{-5}$ moles per gram (Catalyst C) respectively, as compared to Catalyst A.

Formation of Catalyst D

A 3.00 gram sample of 10–30 mesh silica bound GaHZSM-5 was impregnated with a solution containing 3.17 grams of water and 0.20 grams of rhodium nitrate dihydrate. The catalyst was then dried at 120° C. for one hour.

Formation of Catalyst E

Another 3.00 gram sample of Catalyst A was impregnated with 73.5 milligrams of an aqueous solution of perrhenic acid ($HReO_4$) that was 60% Re. The solid was dried in a convection oven at 125° C. and then calcined at 500° C. The resulting catalyst, Catalyst E, contained up to $7.9 \times 10^{-5}$ moles of Re per gram of the bound catalyst. The Re content was determined by chemical analysis to be 1.0% by weight.

Formation of Catalyst 1

Three grams of 0.8% weight Re/GaHZSM-5 was placed in a porcelain crucible. A solution of 3.19 grams of water and 0.029 grams of rhodium nitrate dihydrate was added to the catalyst by impregnation. The sieve was dried for one hour at 120° C. The resulting catalyst was nominally 0.3 weight % Rh.

Formation of Catalyst 2

A 3.00 gram sample of 10–30 mesh silica bound GaHZSM-5 was impregnated with a solution containing 3.17 grams of water and 0.20 grams of rhodium nitrate dihydrate. The catalyst was then dried at 120° C. for one hour. The catalyst was then impregnated with a solution of 2.927 grams of water and 0.031 grams of 85% perrhenic acid solution. The catalyst was then dried at 120° C. for one hour.

Formation of Catalyst 3

Three grams of silica bound 10–30 mesh GaHZSM-5 was placed in a porcelain crucible. A solution of 0.03 grams of 85% perrhenic acid and 2.27 grams of water was impregnated into the solid, which was then dried at 125° C. for one hour. The catalyst was then impregnated with a solution containing 0.016 grams of $[Pt(NH_3)_4](NO_3)_2$, in 2.24 grams of water and dried a second time at 125° C. for one hour.

Formation of Catalyst 4

A 3.00 gram sample of 10–30 mesh silica bound GaHZSM-5 was impregnated with a solution containing 0.016 gram of $[Pt(NH_3)_4](NO_3)_2$ in 2.25 grams of water. The solid was then dried at 150° C. for one hour. The cooled solid was then impregnated with a solution of 0.0335 grams of perrhenic acid (85%) and 2.27 grams of water. The solid was then dried at 150° C. for one hour.

Three grams of each catalyst designated above was tested by being loaded into a quartz reactor and heated under nitrogen to reaction temperature. The catalyst bed was maintained at constant temperature throughout the reaction. Reaction conditions, conversion selectivities and yield are reported in the following table concerning ethane conversion of gallium exchanged HZSM-5 catalysts. The feedstock content was 100% ethane.

Key to Table I

Temp = Temperature, degrees centigrade
wwh = Weight of ethane per weight of catalyst per hour
Time = Hours
Conv = Per pass conversion of ethane
$C_3$–$C_5$ = $C_3$ to $C_5$ hydrocarbons
$C_6+$ = Aromatics exch=exchanged, modified, impregnated Formulas:

$$\text{Conv} = 100 \times \frac{\text{Amt. Ethane Fed(gr)} - \text{Amt. Ethane in Effluent(gr)}}{\text{Amt. Ethane Fed(gr)}}$$

$$\text{Selectivity} = 100 \times \frac{\text{(Amt. of Specific Product in Effluent(gr))}}{\text{(Amt. of Ethane Fed(gr)} - \text{Amt. Ethane in Effluent(gr))}}$$

$$\text{Yield} = \text{Conv} \times \text{Selectivity}$$

TABLE I

Conversion and Selectivity of Promoted GaHZSM-5 Catalysts Over Ethane

| Catalyst | Temp | wwh | Time | Conv | Selectivity | | | | | Yield |
| | | | | | $H_2$ | $CH_4$ | $C_2H_4$ | $C_3C_5$ | $C_6+$ | $C_6+$ |
|---|---|---|---|---|---|---|---|---|---|---|
| A  Ga exch HZSM-5 | 620 | 0.73 | 1.2 | 14.2 | 10.4 | — | 4.2 | 12.6 | 75.0 | 10.6 |
|  | 640 | 0.73 | 1.2 | 19.2 | 9.6 | 7.0 | 3.2 | 11.7 | 76.1 | 14.6 |
| B  Ga exch HZSM-5 | 620 | 0.73 | 1.5 | 13.1 | 13.4 | 13.3 | 15.0 | 5.2 | 52.2 | 6.8 |
| 1% Ga(NO₃)₃ | 640 | 0.73 | 1.0 | 32.5 | 8.1 | 13.1 | 27.8 | 2.1 | 47.4 | 15.4 |
| C  Ga exch HZSM-5 | 620 | 0.73 | 1.2 | 15.9 | 11.6 | 8.0 | 3.7 | — | 73.8 | 11.7 |
| 2% Ga impreg | 640 | 0.73 | 1.0 | 22.9 | 11.1 | 9.9 | 2.8 | 7.5 | 67.6 | 15.5 |
| D  Ga exch HZSM-5 | 615 | 0.73 | 1.7 | 13.4 | 11.1 | 20.8 | 0.0 | 16.4 | 50.0 | 7.7 |
| 2% Rh(NO₃)₃ | 643 | 0.73 | 1.2 | 21.4 | 9.4 | 24.9 | 0.1 | 10.1 | 55.5 | 11.9 |
| E  Ga exch HZSM-5 | 620 | 0.73 | 0.5 | 40.5 | 7.6 | 31.3 | 2.0 | 2.7 | 55.8 | 22.6 |
| 1.0% Re(HReO₄) | 640 | 0.73 | 0.5 | 51.3 | 5.0 | 39.3 | 1.3 | 0.4 | 53.3 | 27.3 |
| 1  Ga exch HZSM-5 | 620 | 0.73 | 0.6 | 46.2 | 8.9 | 23.7 | 0.9 | 6.1 | 60.8 | 28.1 |
| 0.6% Re, 0.3% Rh | 640 | 0.73 | 0.5 | 48.3 | 9.0 | 27.1 | 0.8 | 3.1 | 60.0 | 29.0 |
|  | 620 | 0.73 | 0.5 | 42.5 | 8.7 | 26.3 | 0.6 | 2.8 | 61.6 | 26.2 |
| 2  Ga exch HZSM-5 | 620 | 0.73 | 0.5 | 26.2 | 8.0 | 16.8 | 0.7 | 6.4 | 67.9 | 17.8 |
| 0.3% Rh, 0.6% Re | 640 | 0.73 | 1.0 | 29.4 | 10.4 | 25.8 | 1.0 | 3.8 | 57.2 | 16.8 |
| 3  Ga exch HZSM-5 | 620 | 0.48 | 0.6 | 25.0 | 8.9 | 11.4 | 0.0 | 7.0 | 70.2 | 17.5 |
| 0.6% Re, 0.3% Pt | 640 | 0.73 | 0.5 | 34.9 | 9.0 | 11.5 | 2.5 | 4.3 | 68.1 | 23.8 |
| 4  Ga exch HZSM-5 | 620 | 0.73 | 0.5 | 41.3 | 8.8 | 13.3 | 0.7 | 11.6 | 65.0 | 26.8 |
| 0.3% Pt, 0.6% Re | 640 | 0.73 | 0.9 | 37.5 | 9.4 | 16.2 | 1.1 | 13.1 | 59.5 | 22.3 |

Catalysts A–E represent comparative examples. Catalysts A, B and C are simple gallium exchanged (A) and impregnated (B,C) HZSM-5 catalysts as taught in the art. Catalysts D and E represent the simple catalyst of A–C promoted with rhodium or rhenium as is shown in the art.

Catalysts 1–4 are representative examples of the subject invention, which demonstrate the use of rhenium plus selected metals as promoters. These catalysts exhibit unexpectedly lower methane selectivity, with an increase in hydrogen selectivity. (See Catalyst E and Catalysts 1–4). This results in effective and efficient ethane conversion and increased selectivity to aromatics. Catalyst E, which exhibited a per pass conversion rate comparable to Catalysts 1–4, also exhibited high selectivity to methane and thus lower hydrogen and aromatic selectivities.

Catalyst D, which is a rhodium promoted GaHZSM-5, displayed lower per pass conversion of ethane to aromatics than the GaHZSM-5 catalyst (B,C) alone. Catalyst E, however, which is a rhenium promoted GaHZSM-5 catalyst, exhibited an increase in per pass conversion of ethane to aromatics over that of Catalysts B and C. It would be expected therefore, that a combination rhodium, rhenium promoted GaHZSM-5 catalyst would exhibit somewhat lower per pass conversion of ethane to aromatics than the rhenium catalyst alone. Catalyst 1 which is a rhenium-rhodium promoted catalyst according to the present invention, however, showed an unexpected increase in performance. Catalyst 2, which is a modified version of Catalyst 1, wherein the rhodium metal component was added before the rhenium component, exhibited a moderate improvement in conversion of ethane over that of comparative Catalyst D, but did not achieve the higher conversion achieved by Catalyst 1 where the rhenium component was added first.

Catalysts 3 and 4 represent a platinum-containing catalyst according to the present invention. The platinum component in these catalysts is comparable in function to the rhodium component of Catalysts 1 and 2. Catalyst 3, wherein the rhenium was added before the platinum, achieved good conversion of ethane and selectivity to aromatics. Catalyst 4, however, where the platinum was added prior to the rhenium, exhibited conversion and selectivity rates higher than those of Catalyst 3. This result is unexpected, especially in light of the lower conversion observed with Catalyst 2, where the rhenium was added second, as compared to Catalyst 1, where the rhenium was added prior to the selected metal component, as was done with Catalyst 3.

Catalysts 1, 2 and 4, further demonstrate that operability at the lower temperature, 620° C., results in yields in aromatics comparable to those seen at the higher temperature of 640° C. This is not necessarily true for the comparative examples, A–E, where the data indicates that at decreased temperatures significant decrease in the yield to aromatics is observed.

The foregoing examples demonstrate the enhanced capacity for conversion and selectivity that can be attained by modifying a simple GaHZSM-5 catalyst with rhenium and a metal selected from the group consisting of nickel, palladium, platinum, rhodium and iridium.

It is to be understood that the foregoing examples have been provided to enable those skilled in the art to have representative examples by which to evaluate the invention and that these examples should not be construed as any limitation of the scope of this invention. Thus, it is believed that any of the variables disclosed herein can readily be determined and controlled without departing from the spirit of the invention herein disclosed and described. Moreover, the scope of the invention shall include all modifications, variations and equivalent embodiments that fall within the scope of the appended claims.

What we claim is:

1. A process for the conversion of ehtane to liquid aromatic hydrocarbons comprising contacting, at a temperature of from about 500° C. to about 700° C., an ethane rich feedstock with a catalyst consisting essetially of a gallium modified acid form ZSM-5 or ZSM-11 molecular sieve, promoted with rhenium and a metal selected from the group consisting of nickel, palladium, platinum, rhodium and iridium.

2. The process as in claim 1 wherein said conversion is accomplished at a temperature of from about 575° C. to about 650° C.

3. The process as in claim 1 wherein the gallium is present in an amount of from about 0.1% to about 10% by weight of the total molecular sieve in said catalyst.

4. The process as in claim 1 wherein the rhenium is present in an amount of from about 1.0% to about 10% by weight of the total catalyst.

5. The process as in claim 4 wherein the rhenium is present in an amount of from about 0.4% to about 2% by weight of the total catalyst.

6. The process as in claim 1 wherein said metal is rhodium.

7. The process as in claim 1 wherein said metal is platinum.

8. The process as in claim 1 wherein said metal is present in an amount of from about 0.01% to about 25% by weight of the total catalyst.

9. The process as in claim 8 wherein said metal is present in an amount of from about 0.2% to about 5% by weight of the total catalyst.

10. The process as in claim 1 wherein said molecular sieve has a Si:Al ratio of about 10:1 to about 100:1.

11. The process as in claim 10 wherein said Si:Al ratio is about 20:1 to about 50:1.

12. The process as in claim 1 wherein said catalyst is prepared by
(a) modifying said acid form ZSM-5 or ZSM-11 molecular sieve with gallium; and
(b) incorporating into said molecular sieve rhenium and a metal selected from the group consisting of nickel, palladium, platinum, rhodium and iridium.

13. The process as in claim 12 wherein said modifying is accomplished by at least one of impregnation and ion exchange.

14. The process as in claim 12 wherein said metal is incorporated into said molecular sieve in the form of a metal salt.

15. The process as in claim 14 wherein said metal salt is $Rh(NO_3)_3 \cdot 2H_2O$.

16. The process as in claim 12 wherein said metal is incorporated into said molecular sieve in the form of a complex cation salt.

17. The process as in claim 16 wherein said complex cation salt is $[Pt(NH_3)_4](NO_3)_2$.

18. The process as in claim 16 wherein said complex cation salt is $[Pt(NH_3)_4](2Cl)_2$.

19. The process as in claim 12 wherein said metal is platinum and the platinum is incorporated into said molecular sieve prior to the addition of the rhenium.

* * * * *